(12) United States Patent
Terrell et al.

(10) Patent No.: US 10,363,145 B2
(45) Date of Patent: Jul. 30, 2019

(54) LATERAL PLATE AND SPINAL IMPLANT SYSTEM AND METHOD

(71) Applicant: Amendia, Inc., Marietta, GA (US)

(72) Inventors: Reginald Antonio Terrell, Marietta, GA (US); Lauren Chase Thornburg, Atlanta, GA (US); Timothy Spencer, Battle Creek, MI (US)

(*) Notice: Subject to any disclaimer, the term of this patent is extended or adjusted under 35 U.S.C. 154(b) by 630 days.

(21) Appl. No.: 15/049,434

(22) Filed: Feb. 22, 2016

(65) Prior Publication Data
US 2016/0242925 A1  Aug. 25, 2016

Related U.S. Application Data

(60) Provisional application No. 62/119,406, filed on Feb. 23, 2015.

(51) Int. Cl.
*A61B 17/70* (2006.01)
*A61F 2/44* (2006.01)
*A61B 17/80* (2006.01)

(52) U.S. Cl.
CPC .......... *A61F 2/447* (2013.01); *A61B 17/7059* (2013.01); *A61B 17/8047* (2013.01); *A61B 17/8004* (2013.01); *A61B 17/8042* (2013.01); *A61F 2002/4475* (2013.01); *A61F 2220/0041* (2013.01)

(58) Field of Classification Search
CPC .... A61F 2/445; A61F 2/447; A61F 2002/443; A61F 2002/4435; A61F 2002/4475; A61B 17/8038; A61B 17/8042; A61B 17/8047; A61B 17/7044; A61B 17/7059
See application file for complete search history.

(56) References Cited

U.S. PATENT DOCUMENTS

| 5,487,743 | A | * | 1/1996 | Laurain | ................ | A61B 17/70 606/261 |
|---|---|---|---|---|---|---|
| 6,235,034 | B1 | | 5/2001 | Bray | | |
| 6,413,259 | B1 | | 7/2002 | Lyons et al. | | |
| 7,452,370 | B2 | | 11/2008 | Anderson | | |
| 8,273,127 | B2 | | 9/2012 | Jones et al. | | |
| 8,348,982 | B2 | | 1/2013 | Baynham | | |
| 8,709,085 | B2 | | 4/2014 | Lechmann et al. | | |
| 9,463,097 | B2 | * | 10/2016 | Lechmann | ............. | A61B 17/86 |
| 9,943,417 | B2 | * | 4/2018 | Laurence | ............. | A61F 2/4465 |
| 2002/0111630 | A1 | * | 8/2002 | Ralph | ................ | A61B 17/7059 606/71 |
| 2012/0277873 | A1 | | 11/2012 | Kana et al. | | |
| 2014/0012380 | A1 | | 1/2014 | Laurence et al. | | |

* cited by examiner

*Primary Examiner* — Anu Ramana

(57) ABSTRACT

A lateral plate assembly has an elongated lateral plate for attachment to adjacent vertebrae having a first end portion and a second end portion and a pair of apertures for receiving a first and a second bone screw. The pair of apertures includes a first aperture which is an opening positioned in the first end portion for receiving the first bone screw and a second aperture which is a slotted opening to receive the second bone screw. The second end portion of the lateral plate has an open end with channelled internal sides for receiving and holding a moveable washer on top of the slotted opening. The washer is configured to move along a length of the slotted aperture. The moveable washer has an opening for holding a head of the second bone screw. Movement of the washer relative to the slotted opening increases or decreases the distance between locations of the respective screw heads.

22 Claims, 8 Drawing Sheets

LATERAL PLATE AND SPINAL IMPLANT SYSTEM AND METHOD

TECHNICAL FIELD

The present invention relates to a lateral plate fixation device for spinal column repair and stabilization. The device, when coupled to an implant cage or body for spinal fusion, creates a spinal implant system.

BACKGROUND OF THE INVENTION

Spinal implant fusion systems are well known and widely used to correct abnormalities and alignment issues between adjacent vertebrae.

The goal in providing such a repair is to minimize the trauma to the surrounding tissue and nerves when implanting the device. The least amount of disruption to the patient's anatomy while correcting the defect while providing stabilization between the adjacent vertebral bodies is the goal in any surgical repair procedure.

The present invention described hereinafter provides this capability while giving the surgeon the ability to adjust the attachment locations relative to the bone structure of the vertebral bodies to achieve a more secure fixation by varying the angulation and screw placement used to anchor the device in place.

SUMMARY OF THE INVENTION

A lateral plate assembly has an elongated lateral plate for attachment to adjacent vertebrae having a first end portion and a second end portion and a pair of apertures for receiving a first and a second bone screw. The pair of apertures includes a first aperture which is an opening positioned in the first end portion for receiving the first bone screw and a second aperture which is a slotted opening to receive the second bone screw. The second end portion of the lateral plate has an open end with channelled internal sides for receiving and holding a moveable washer on top of the slotted opening. The washer is configured to move along a length of the slotted aperture. The moveable washer has an opening for holding a head of the second bone screw. Movement of the washer relative to the slotted opening increases or decreases the distance between locations of the respective screw heads.

The lateral plate assembly may further include a threaded third aperture on the lateral plate interposed between the first and second aperture, an anti-back out mechanism assembly and an attachment fastener. The anti-back out mechanism assembly has a locking tab with an externally threaded screw and a locking ring, wherein the threaded screw is locked to an aperture of the locking tab and the external thread of the screw engages the threaded third aperture of the lateral plate. The two bone screws when fastened to the vertebrae are prevented from back out by the anti-back out fastener as the locking tab projects over at least portions of heads of each bone screw. The attachment fastener fixes the elongated plate to an implant body. The attachment fastener extends through a central opening of the externally threaded screw to fix the implant body to the lateral plate.

Preferably, the elongated lateral plate has a low profile thickness. The thickness of the lateral plate can be in the range of 3 mm to 5 mm, preferably the lateral plate thickness is 4 mm. The lateral plate has a maximum width at the second end of 20 mm or less, preferably the maximum width is 15 mm.

The anti-back out mechanism assembly lies in a recess in the lateral plate and extends over at least partially the first opening and second slotted opening. The anti-back out mechanism assembly has an outer surface that is flush or below relative to an outer surface of the lateral plate when tightened into the recess.

The bone screws each have polyaxial heads adapted to be flush or below the lateral plate when in the respective first opening or the washer covered second slotted opening when tilted on an angle in the range of −2 degrees toward interior or center of the lateral plate to +5 degrees toward the ends of the lateral plate yielding a total screw angulation of −4 degrees to 10 degrees between the screws when the screw heads are flush. The first and second screw can have a larger upper range of angulation of −2 degrees to +15 degrees each yielding a maximum upper range of angulation between screws of +30 degrees when the screw heads are allowed to project slightly above the openings and the lateral plate.

The elongated lateral plate can be combined with an implant body to form a spinal implant assembly. The implant body is for insertion between adjacent vertebral bodies. The body has an upper load supporting surface and a lower load supporting surface spaced by walls. The walls include a pair of opposing sidewalls and a proximal end wall and a distal end wall. The proximal end wall has a threaded aperture. The elongated lateral plate has a first end portion and a second end portion and a pair of apertures for receiving a first and a second bone screw, a first aperture having an opening positioned in the first end portion for receiving and holding the first bone screw and a second aperture having a slotted opening to receive the second bone screw. The apertures for receiving first and second bone screws are positioned spaced from an interposed threaded third aperture for alignment with the thread aperture of the implant body. An attachment fastener fixes the elongated lateral plate to the implant body at the threaded apertures.

The spinal implant assembly may further have the anti-back out mechanism assembly having a locking tab with an externally threaded washer and a locking ring.

BRIEF DESCRIPTION OF THE DRAWINGS

The invention will be described by way of example and with reference to the accompanying drawings in which:

FIG. 5A showing negative inclinations. FIG. 5B showing positive inclinations, views 5A and 5B both having flush screw heads. FIG. 5C showing maximum inclinations with projecting screw heads.

FIG. 7A is a bottom plan view of the lateral plate assembly of the present invention without an implant body. FIG. 7B is an end plan view showing a close end portion of the lateral plate assembly. FIG. 7C is a side plan view. FIG. 7D is the opposite end view showing the moveable washer. FIG. 7E is a top plan view. FIG. 7F is a top perspective view.

DETAILED DESCRIPTION OF THE INVENTION

Figure 1:
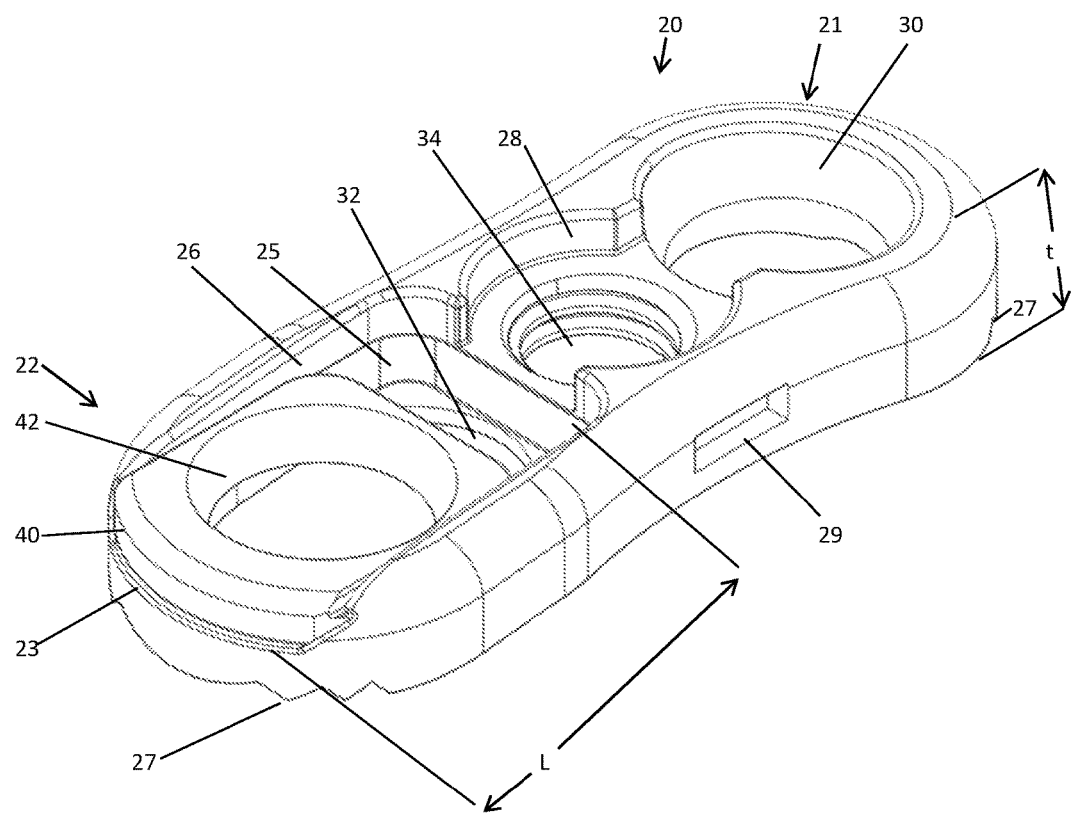
FIG. 1 is a perspective view of the lateral plate of the present invention with the moveable washer.
Figure 2:
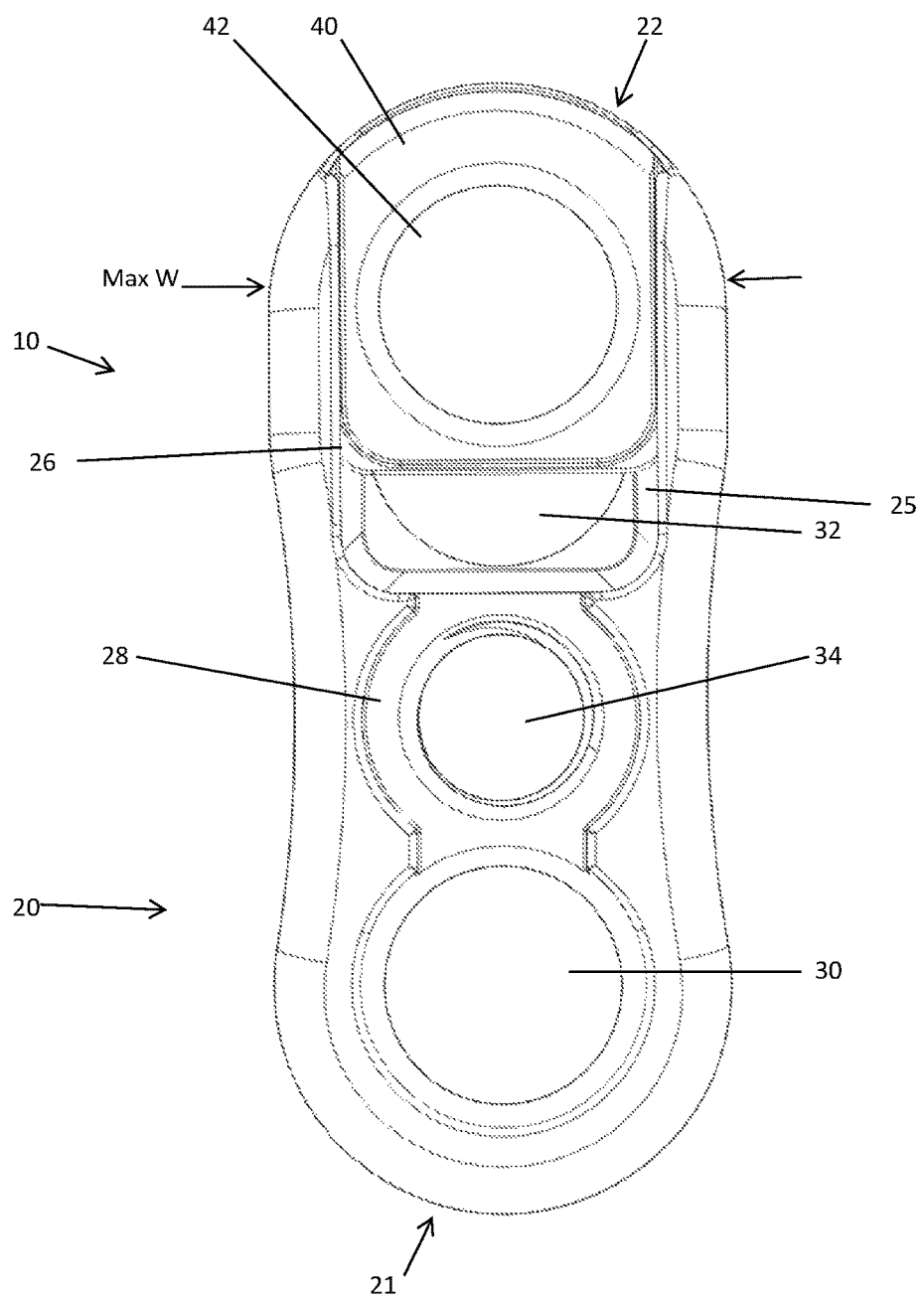
FIG. 2 is a top plan view of the lateral plate taken from FIG. 1.

A lateral plate assembly 10 is illustrated in FIGS. 1, 2, 3, 5A-C, 7A-F. In this particular embodiment, the lateral plate assembly 10 includes an elongated lateral plate 20 and a moveable washer 40, as illustrated in FIGS. 1 and 2 and in the exploded view of FIG. 3. This elongated lateral plate 20 is for attachment to adjacent vertebrae 2, 4 as illustrated in FIG. 8. The lateral plate 20 has a first closed end portion 21 and a second closed end portion 22. Each closed end portion 21, 22 has an aperture for receiving a bone screw. The first aperture 30 is a circular opening 30 that can be hemispherical or frustoconical for receiving the head 61 of a bone screw 60 positioned in the first closed end portion 21. The second closed end portion 22 has the second aperture which is a slotted opening 32 for receiving the second bone screw 62 as illustrated. The slotted opening 32 extends from the second closed end portion 22 which has an open end 23 with channeled internal grooves 25 and overhanging lips 26 above the second closed end portion 22 for receiving and holding a moveable washer 40 on top of the slotted opening 32. The washer 40 fits into channels or grooves 25 cut into the plate 20 while overhanging lips 26 hold the washer in place. This washer 40 is configured to move along the length L above the slotted opening 32. The moveable washer 40 has an opening 42 for receiving a head 61 of bone screw 62. This opening 42 can be made similar to that of the frustoconical opening 30 of the opposite end of the lateral plate 20 and may have a similar frustoconical or hemispherical configuration adapted to receive a polyaxial screw that it can be angulated.

The slotted opening 32 allows the washer 40 to move along the length L such that it can increase or decrease the distance between the locations of the respective screw heads 61 of the screws 60, 62. This ability to move the screw heads 61 along the length of the elongated lateral plate 20 enables the surgeon to ideally locate the screws 60, 62 relative to the bone structure which he intends to drive the bone screws into and in so doing he can adjust or vary the compressive alignment forces on the vertebral bodies.

With reference to the center of the elongated lateral plate 20, there is illustrated a third aperture 34 in a recess 28. This aperture 34 is threaded and will be discussed later as a means for attaching the bone plate either to a spinal implant body and also to secure an anti-back out mechanism which will be discussed hereinafter.

Along the bottom surface of the lateral plate 20, as illustrated in FIGS. 1 and 2, one will see serrations 27. These serrations 27 help grip against the bone structure. As illustrated, the elongated lateral plate 20 has a thickness t and, as illustrated in FIG. 2, has a maximum width W at the open end of the lateral plate 20. Along each side of the lateral plate 20 is a slot or recess 29 to hold onto the plate 20 with a forceps or similar device.

Figure 3:
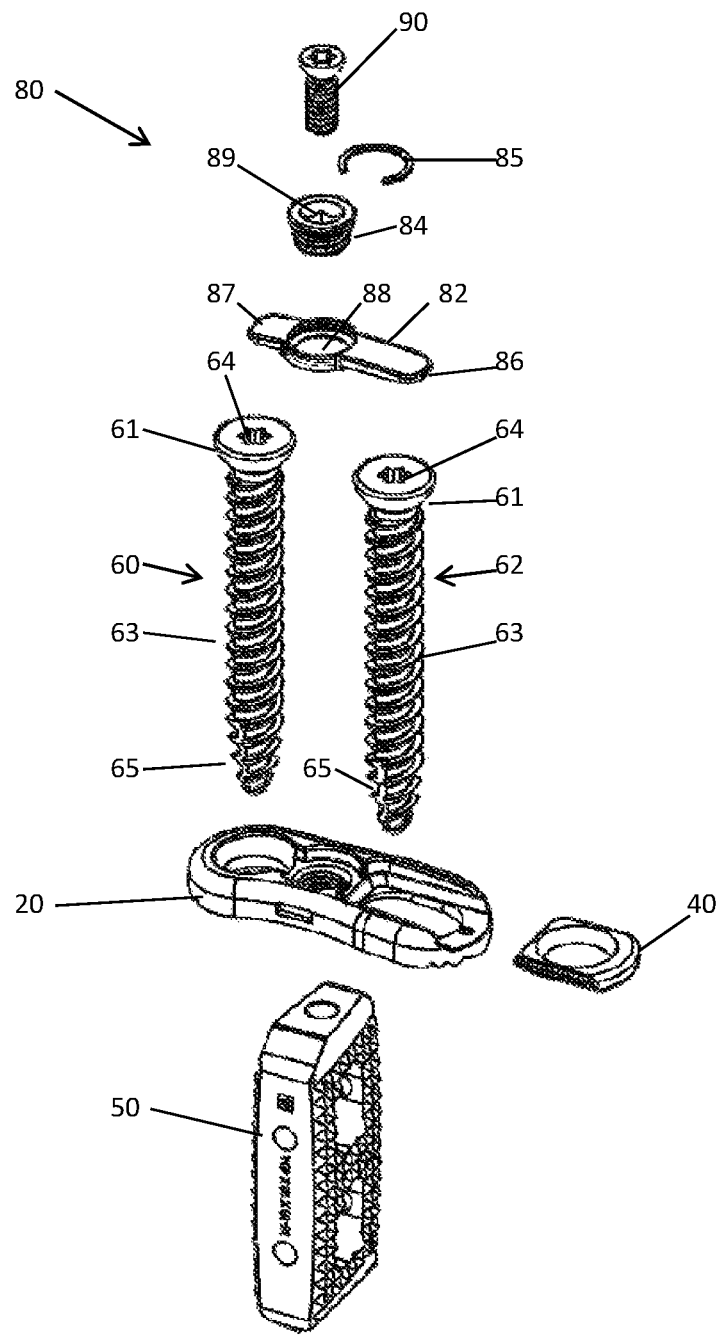
FIG. 3 is an exploded view of the spinal implant device with the lateral plate and moveable washer and the anti-back out mechanism and two bone screws and an implant body or cage made according to one embodiment of the present invention.

With further reference to FIG. 3, the exploded view of the lateral plate assembly 20 with an additional component. This additional component is a spinal implant body or cage 50.

This implant body 50 can be used with the lateral plate assembly 10 in such a fashion that the lateral plate 20 can be secured to this implant body 50. Above the lateral plate 20 and washer 40 is shown the pair of bone screws 60 and 62. As discussed, the bone screws 60, 62 have heads 61 adapted to fit in the apertures or openings 30, 32. Each bone screw 60, 62 has a shank 63 that is threaded. As shown, these bone screws 60, 62 also have cutting flutes 65 that enable penetration into the bone as the bone screw is being threaded into bone. The heads 61 of the bone screws 60, 62 have fastening apertures 64 to allow a tool to be inserted to provide torsional forces to drive the screw 60 or 62 into positon into the bones. Above the bone screws 60, 62 as illustrated is the anti-back out mechanism 80. The anti-back out mechanism 80 includes a locking tab 82 having projecting ears 86 and 87. The ear 86 being elongated. This ear 86 will fit over the washer 40 and the slotted opening 32 as seen in the exploded view. A center aperture 88 is provided into which a screw 84 can be inserted. This screw 84 is held in place by the use of a snap ring 85 to complete the mechanism 80. As shown, this screw 84 includes an opening 89 into which a fastener 90 can be provided. The fastener 90 when tightened secures the plate assembly to the implant body 50. This is best illustrated in FIGS. 5A-C and also all the FIGS. 7A-7F.

Figure 5A:
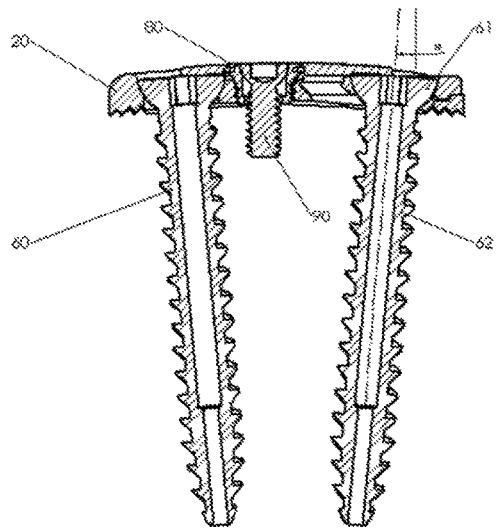
FIGS. 5A-5C are cross sectional views of the lateral plate assembly and the two bone screws.
Figure 5B:
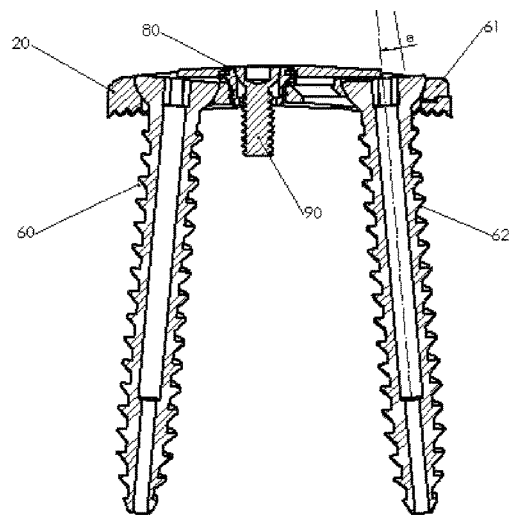
Figure 5C:
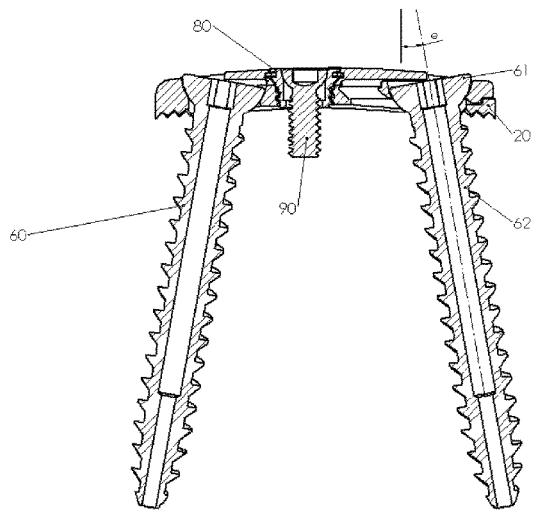

With reference to FIGS. 5A, 5B and 5C, an important aspect of the invention is that the apertures 30, 32 and opening 42 allow the heads 61 of the screws 60, 62 to be angulated relative to a vertical plane. This angulation θ can have the bone screws 60, 62 tilted inwardly relative to the plate such that a −2 degree inclination can be achieved where the points of the screws 60, 62 are directed towards each as illustrated in FIG. 5A. In FIG. 5B, the screws 60, 62 alternatively can be angulated on a positive angle θ. This angle of inclination can achieve up to 5 degrees wherein the points are directed outwardly. When inclined at these angles, the heads 61 of the bone screw 60, 62 as illustrated remain flush with the elongated plate 20 such that they do not protrude above the plate 20 at any portion of the plate. This is extremely interesting in that the objective or goal is to keep the bone plate 20 as flush as possible against the vertebrae into which it is to be attached. As previously discussed, the plate 20 can have a thickness of 5 mm to 3 mm, preferably about 4 mm. When the bone screws 60, 62 are angulated in such a fashion that they remain flush, this thickness is never exceeded during the assembly. With reference to FIG. 5C it is noted that the positive inclination can actually be extended so that each screw 60, 62 can be inclined as much as 15 degrees in the positive direction. As shown, this results in portions of the head 61 of the screw 60, 62 extending past the structure of the lateral plate 20 and leaves small portions of the head 61 protruding outwardly. While this is not preferred, it is possible to be done giving the surgeon a wider range of angles of which to properly place the bone screw 60, 62 when he is driving it into the adjacent vertebrae 2, 4 as illustrated in FIG. 8.

Figure 7A:
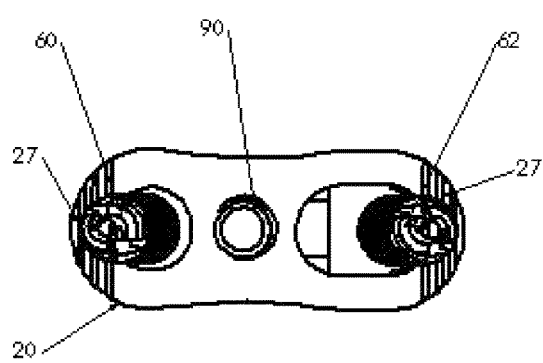
FIGS. 7A-7F are various views of the lateral plate assembly of a first embodiment.
Figure 7B:
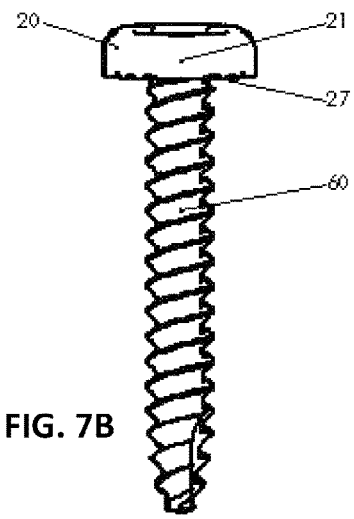
Figure 7C:
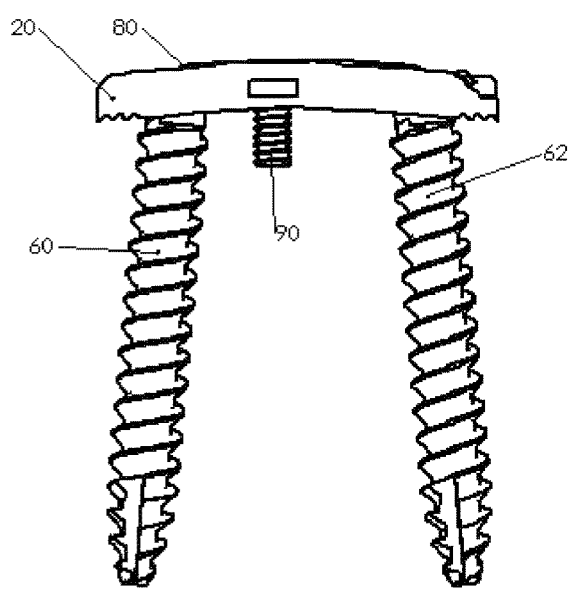
Figure 7D:
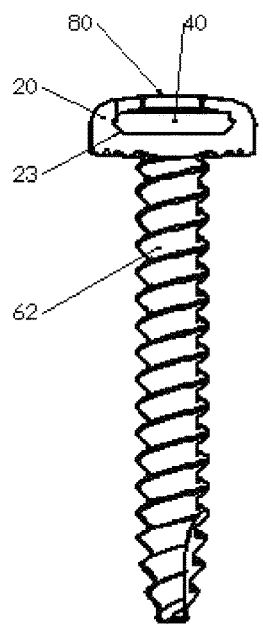
Figure 7E:
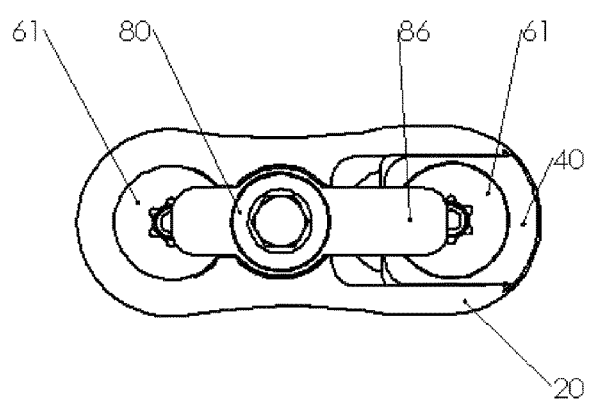
Figure 7F:
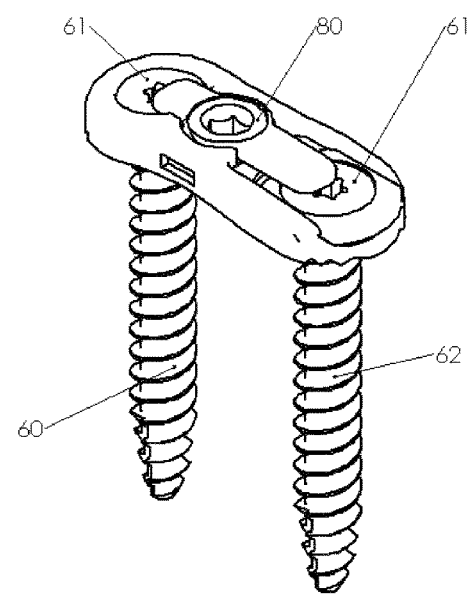
Figure 8:
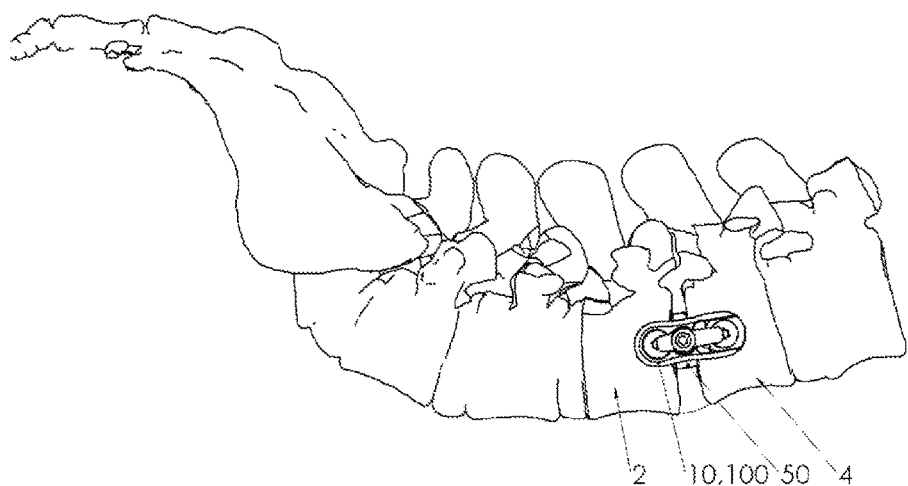
FIG. 8 is a perspective exemplary view of the lateral plate assembly shown affixed to a portion of a spine.

With reference to FIG. 7A, a bottom view of the bone screws 60, 62 is illustrated having been inserted and inclined in a positive inclination with regard to the vertical direction. At each end of the plate 20 are shown the serrations 27 for biting into the vertebral body and preventing any slippage against the vertebral bodies once the bone screws 60, 62 are properly affixed. In FIG. 7B, a closed end 21 of the lateral plate 20 is shown where the bone screws 60, 62 are facing vertically downwardly. With reference to FIG. 7C, a side view is shown wherein the fastener 90 is shown projecting downwardly and the anti-back out mechanism 80 is shown properly positioned over the tops of the screws 60, 62. FIG. 7D shows an opposite end 22 view showing the open end 23 exposing the moveable washer 40 so that it can be seen in its secured and locked position under the anti-back out mechanism 80. FIG. 7E shows a top view with the anti-back out mechanism 80 shown partially extending over the heads 61 of the screws 60, 62; this prevents the screws from backing out as previously discussed. FIG. 7F shows a perspective view of this embodiment.

Figure 4A:
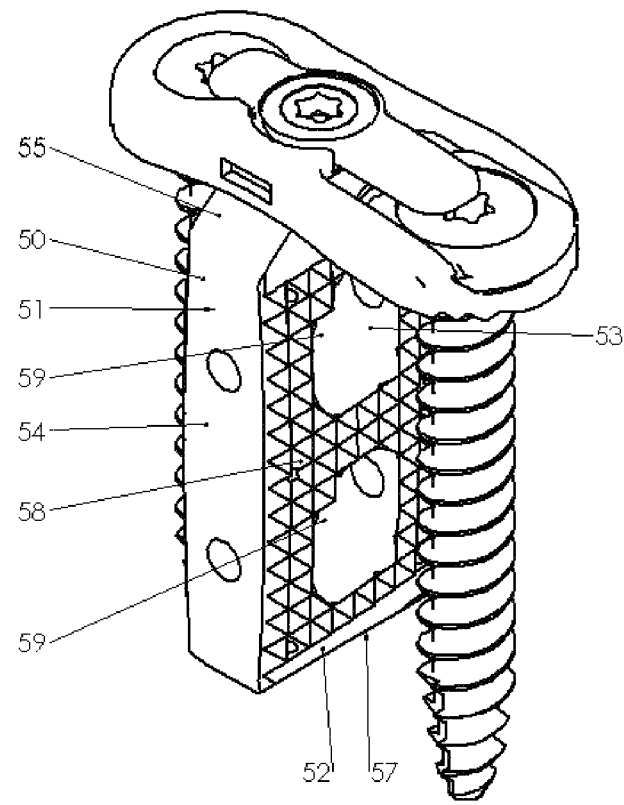
FIG. 4A is a perspective view of the assembly of the spinal implant of FIG. 3.
Figure 4B:
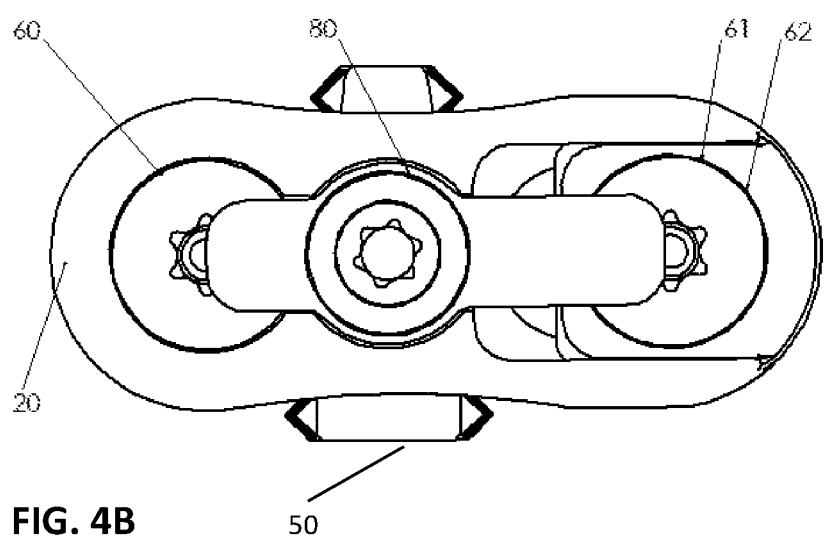
FIG. 4B is a top view of the spinal implant taken from FIG. 4A.

In a second embodiment, the lateral plate assembly is combined with an implant body or cage 50 to form a system 100 which is illustrated in FIG. 3 in the exploded view and FIGS. 4A, 4B and FIGS. 6A-6E. The implant body or cage 50 is illustrated. This implant body 50 is for insertion between the adjacent vertebral bodies 2 and 4. The body 50 has an upper loading support surface 52 and a lower supporting surface 54 spaced by walls including a pair of opposing side walls 51, 53 and a proximal end wall 55 and a distal end wall 57. The proximal end wall 55 has a threaded aperture 56. As shown in FIG. 4A, between the walls can be cavities or spaces 59 as illustrated. These spaces 59 can allow for autograft material or allograft material to be positioned inside the implant body 50 to facilitate fusion of the implant body 50 to the adjacent vertebrae 2, 4. As shown, the supporting load surfaces 52, 54 can be faceted having a plurality of projections 58 for biting into the bone structure of the adjacent vertebrae 2, 4 when implanted. The lateral plate 20 can be an implantable metal such as titanium or stainless steel and the implant 50 can be a polymer like polyether ether ketone (PEEK) or its equivalent.

Figure 6A:
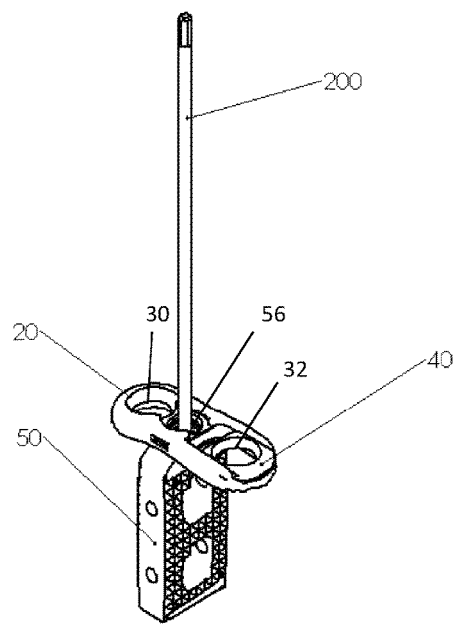
FIGS. 6A-6E show sequential steps of implantation and fixation methodology of the spinal implant of the present invention utilizing a rod and a guide.
Figure 6B:
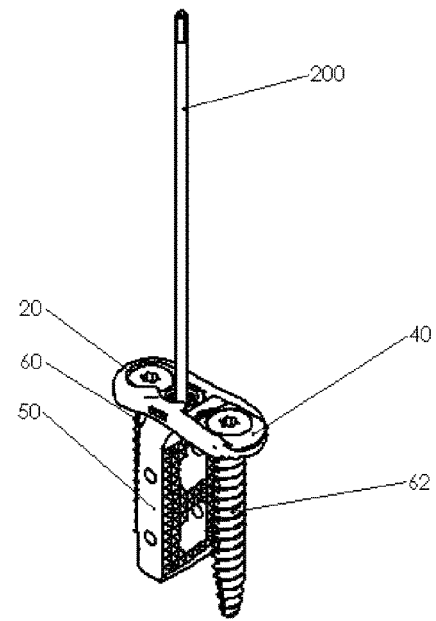
Figure 6C:
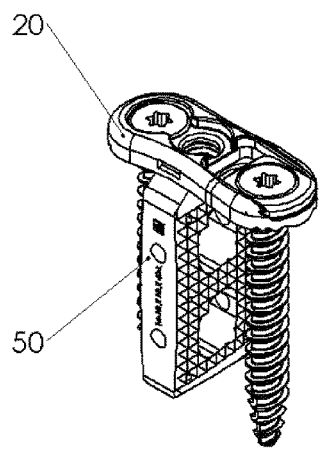
Figure 6D:
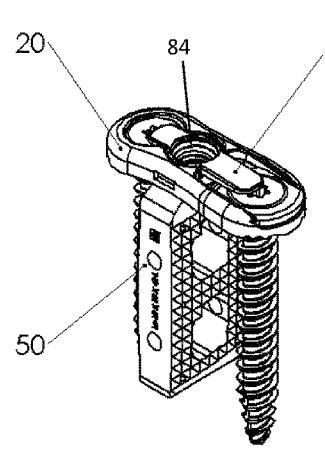
Figure 6E:
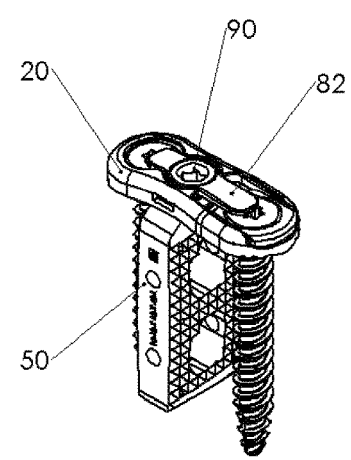

To better understand how the present invention can be employed between two adjacent vertebrae using a lateral approach is shown in FIG. 8. The assembly 10 when used with an implant body 50 is illustrated. Initially, the surgeon will fasten the implant body 50 through the threaded aperture 56 and in doing so secures the implant body 50 firmly against the threaded rod 200, as shown in FIG. 6A. At this point as shown in FIG. 6B, the two bone screws 60 and 62 can be dropped into the apertures 30, 32. Thereafter, the tab 82 can be positioned into the aperture in plate 20. At this point the screw 84 contained in the anti-back out mechanism 80 can be locked into position. At this point, the assembly 100 is shown with the anti-back out mechanism 80 in position as shown in FIG. 6D. Once the bone screws 60, 62 are securely tightened, the fastener 90 can be positioned as shown in FIG. 6E. At this point, the entire assembly 100 is complete and the spinal implant system 100 can be properly positioned and secured to the vertebrae 2, 4 as illustrated in FIG. 8. As noted in FIG. 8, the implant body 50 is provided and spaced between the adjacent vertebrae 2, 4. These and other variations can be accomplished with the present invention.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A lateral plate assembly comprising:
    an elongated lateral plate for attachment to adjacent vertebrae having a first closed end portion and a second closed end portion, a top surface and a bottom surface, and a pair of apertures, a first aperture extending through the top surface and the bottom surface, a second aperture communicating with a slot and positioned in a first surface below the top surface and extending through the bottom surface, the first aperture having an opening positioned in the first closed end portion for receiving a first bone screw and the second aperture communicating with the slot to receive a second bone screw, the slot extending toward the second closed end portion, the second closed end portion being defined by an open end above the second closed end portion; and
    wherein the open end and a pair of sides with grooves and overhanging lips is configured for receiving and holding a moveable washer on top of the second aperture communicating with the slot, the washer after being slid through the open end being configured to move along a length of the second aperture communicating with the slot, the moveable washer having an inner surface defining an opening, a head of the second bone screw held by the inner surface, movement of the washer relative to the second aperture communicating with the slot increases or decreases the distance between locations of a head of the first bone screw and the head of the second bone screw.

2. The lateral plate assembly of claim 1 further comprises:
    a threaded third aperture positioned in a second surface below the top surface of the lateral plate interposed between the first aperture and second aperture communicating with the slot;
    an anti-back out mechanism assembly having a locking tab, an externally threaded third screw and a locking ring, wherein the externally threaded third screw is locked to an aperture of the locking tab by the locking ring and the external thread of the externally threaded third screw is configured to engage the threaded third aperture of the lateral plate and wherein the first and second bone screws when fastened to the vertebrae are prevented from back out by the anti-back out mechanism assembly as the locking tab projects over at least portions of heads of each bone screw; and
    an attachment fastener for fixing the elongated plate to an implant body, the attachment fastener extends through a central opening of the externally threaded third screw and threads into a threaded opening of the implant body to fix the implant body to the lateral plate.

3. The lateral plate assembly of claim 2 wherein the lateral plate has a maximum width at the second closed end portion of 20 mm or less.

4. The lateral plate assembly of claim 3 wherein the maximum width is 15 mm.

5. The lateral plate assembly of claim 4 wherein the anti-back out mechanism assembly extends over at least partially the first aperture and second aperture communicating with the slot.

6. The lateral plate assembly of claim 5 wherein the anti-back out mechanism assembly has an outer surface that is flush or below relative to an outer surface of the lateral plate when tightened.

7. The lateral plate assembly of claim 1 wherein the elongated lateral plate has a low profile thickness.

8. The lateral plate assembly of claim 7 wherein the thickness of the lateral plate is in the range of 3 mm to 5 mm.

9. The lateral plate assembly of claim 8 wherein the lateral plate thickness is 4 mm.

10. The lateral plate assembly of claim 1 wherein the bone screws each have polyaxial heads adapted to be flush or below the lateral plate when in the respective first aperture or the washer opening when tilted on an angle in the range of −2 degrees toward interior or center of the lateral plate or +5 degrees toward the ends of the lateral plate yielding a total screw angulation of −4 degrees to 10 degrees between the screws when the heads of the bone screws are flush.

11. The lateral plate assembly of claim 1 wherein the first and second bone screws can have an angulation of −2 degrees to +15 degrees each yielding a maximum angulation between screws of 30 degrees.

12. A spinal implant assembly comprises:
  an implant body for insertion between adjacent vertebral bodies, the body having an upper load supporting surface and a lower load supporting surface spaced by walls, the walls including a pair of opposing sidewalls and a proximal end wall and a distal end wall, the proximal end wall having a threaded aperture;
  an elongated lateral plate having a first closed end portion and a second closed end portion, a top surface and a bottom surface, and a pair of apertures, a first aperture extending through the top surface and the bottom surface, a second aperture communicating with a slot and positioned in a surface below the top surface and extending through the bottom surface, the first aperture having an opening positioned in the first closed end portion for receiving a first bone screw and the second aperture communicating with the slot to receive a second bone screw, the slot extending toward the second closed end portion, the second closed end portion being defined by an open end above the second close end portion, wherein the apertures for receiving the first and the second bone screws are positioned spaced from an interposed threaded third aperture for alignment with the threaded aperture of the implant body; and
  an attachment fastener for fixing the elongated lateral plate to the implant body at the threaded aperture of the implant body; and
  wherein the open end and a pair of sides with grooves and overhanging lips is configured for receiving and holding a moveable washer on top of the second aperture communicating with the slot, the washer being configured to move along a length of the second aperture communicating with the slot, the moveable washer having an inner surface defining an opening, a head of the second bone screw held by the inner surface, movement of the washer relative to the second aperture communicating with the slot increases or decreases the distance between locations of a head of the first bone screw and the head of the second bone screw.

13. The spinal implant assembly of claim 12 further comprises:
  an anti-back out mechanism assembly having a locking tab, an externally threaded third screw and a locking ring, wherein the externally threaded third screw is locked to an aperture of the locking tab by the locking ring and the external thread of the externally threaded third screw is configured to engage the threaded third aperture of the lateral plate and wherein the first and the second bone screws when fastened to the vertebrae are prevented from back out by the anti-back out mechanism assembly as the locking tab projects over at least portions of the heads of each bone screw, and the attachment fastener extends through a central opening of the externally threaded third screw and threads into a threaded opening of the implant body to fix the elongated lateral plate and implant body.

14. The lateral plate assembly of claim 12 wherein the elongated lateral plate has a low profile thickness.

15. The lateral plate assembly of claim 14 wherein the thickness of the lateral plate is in the range of 3 mm to 5 mm.

16. The lateral plate assembly of claim 15 wherein the lateral plate thickness is 4 mm.

17. The lateral plate assembly of claim 12 wherein the lateral plate has a maximum width at the second closed end portion of 20 mm or less.

18. The lateral plate assembly of claim 17 wherein the maximum width is 15 mm.

19. The lateral plate assembly of claim 18 wherein an anti-back out mechanism assembly extends over at least partially the first aperture and second aperture communicating with the slot.

20. The lateral plate assembly of claim 19 wherein the anti-back out mechanism assembly has an outer surface that is flush or below relative to an outer surface of the lateral plate when tightened.

21. The lateral plate assembly of claim 12 wherein the bone screws each have polyaxial heads adapted to be flush or below the lateral plate when in the respective first aperture or the washer opening when tilted on an angle in the range of −2 degrees toward interior or center of the lateral plate or +5 degrees toward the ends of the lateral plate yielding a total screw angulation of −4 degrees to 10 degrees between the screws when the heads of the bone screws are flush.

22. The lateral plate assembly of claim 12 wherein the first and second bone screws can have an angulation of −2 degrees to +15 degrees each yielding a maximum angulation between screws of 30 degrees.

\* \* \* \* \*